United States Patent [19]

Loewe et al.

[11] 3,996,369

[45] Dec. 7, 1976

[54] ANTHELMINTICALLY ACTIVE 2-CARBALKOXYAMINO BENZIMIDAZOLYL-5(6)-SULFONIC ACID PHENYL ESTERS

[75] Inventors: Heinz Loewe, Kelkheim, Taunus; Josef Urbanietz, Schwalbach, Taunus; Dieter Duwel, Hofheim, Taunus; Reinhard Kirsch, Niederjosbach, Taunus, all of Germany

[73] Assignee: Hoechst Aktiengesellschaft, Frankfurt am Main, Germany

[22] Filed: Aug. 26, 1975

[21] Appl. No.: 608,014

[30] Foreign Application Priority Data

Aug. 28, 1974 Germany ............... 2441202

[52] U.S. Cl. .................. 424/273; 260/309.2; 260/456 A
[51] Int. Cl.² .......................... C07D 235/32
[58] Field of Search ........... 260/309.2; 424/273

[56] References Cited

UNITED STATES PATENTS

| 3,929,821 | 12/1975 | Beard et al. ............ 260/309.2 |
| 3,929,824 | 12/1975 | Beard et al. ............ 260/309.2 |

FOREIGN PATENTS OR APPLICATIONS

| 809,234 | 6/1974 | Belgium ............ 260/309.2 |

*Primary Examiner*—Natalie Trousof
*Attorney, Agent, or Firm*—Curtis, Morris & Safford

[57] ABSTRACT

2-Carbalkoxyamino-benzimidazolyl-5(6)-sulfonic acid phenyl esters are disclosed as well as a process for their manufacture. The new compounds have valuable chemotherapeutic properties and are suitable for combating diseases caused by parasites in humans and animals, such as helminths and liver flukes.

11 Claims, No Drawings

ANTHELMINTICALLY ACTIVE 2-CARBALKOXYAMINO BENZIMIDAZOLYL-5(6)-SULFONIC ACID PHENYL ESTERS

This invention relates to anthelmintically active 2-carbalkoxyamino-benzimidazolyl-5(6)-sulfonic acid phenyl esters and to a process for their manufacture.

2-Carbalkoxy-amino-benzimidazolyl derivatives carrying alkyl, acyl, phenoxy and phenylthio groups in the 5(6)-position are known to possess anthelmintic properties (P. Actor et al., Nature 215, 321 (1967); German Offenlegungsschrift Nos. 2,029,637; 2,264,690 and 2,363,348).

This invention relates to anthelmintically active 2-carbalkoxyamino-benzimidazolyl-5(6) sulfonic acid phenyl esters of the formula (1)

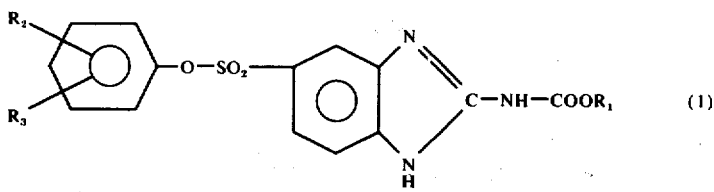

in which $R_1$ stands for alkyl having 1 to 4 carbon atoms, $R_2$ and $R_3$, independently of each other, each stand for hydrogen, hydroxy, alkoxy having 1 to 4 carbon atoms, halogen, trifluoromethyl, alkyl having 1 to 4 carbon atoms, carbalkoxy having 1 to 4 carbon atoms in the alkoxy moiety, or cyano.

The alkyl groups represented by $R_1$, $R_2$ and $R_3$ are methyl, ethyl, propyl, isopropyl, butyl, secondary butyl, and tertiary butyl. The alkoxy groups represented by $R_2$ and $R_3$ are methoxy, ethoxy, propoxy, isopropoxy and butoxy. The halogen atoms represented by $R_2$ and $R_3$ are fluorine, chlorine, bromine and iodine atoms. The carbalkoxy groups represented by $R_2$ and $R_3$ are carbomethoxy, carbo-ethoxy, carbopropoxy or carbobutoxy.

Especially preferred compounds of formula (I) are those, in which $R_1$ stands for methyl, $R_2$ stands for hydrogen, and $R_3$ stands for hydrogen, chlorine, bromine, trifluoromethyl, methyl, ethyl, methoxy or ethoxy, the especially preferred position of the substituents represented by $R_3$ being the 3-position of the phenyl ring.

This invention further relates to a process for the manufacture of 2-carbalkoxyamino-benzimidazolyl-5(6)-sulfonic acid phenyl esters of formula (1) specified above, which comprises condensing an o-phenylene diamine derivative of the formula (2)

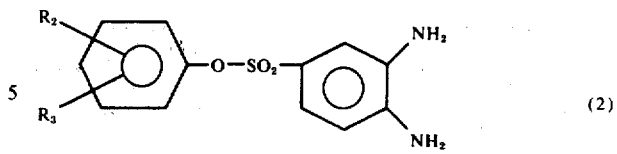

in which $R_2$ and $R_3$ are defined as above, a. with an alkyl-S-methyl-thiourea carboxylate of the formula (3)

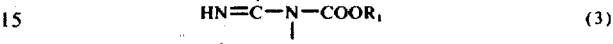

in which $R_1$ is defined as above, or b. with a cyanamide carboxylate of the formula (4)

in which $R_1$ is defined as above, in both cases at a pH-value ranging from 1 to 6, preferably from 2 to 5, or c. reacting it with an N-dichloromethylene carbamic acid ester of the formula (5)

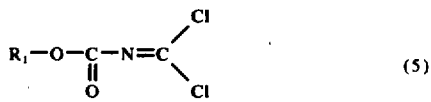

in which $R_1$ is defined as above, at a temperature of from $-10°$ to $+40°$ C in the presence of a base, or d. reacting it with a bis-alkyl or bis-aryl-thio-methylene-amino-formiate of the formula (6)

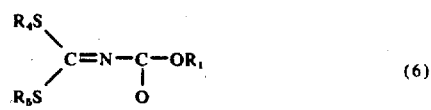

in which $R_1$ is defined as above, and $R_4$ and $R_x$, which may be the same or different, each strand for alkyl having 1 to 4 carbon atoms, alkenyl having 3 to 5 carbon atoms, cyclohexyl, or an optionally substituted phenyl or benzyl group of the formula (7) or (8)

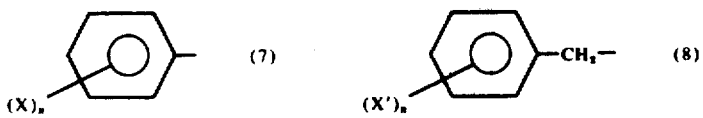

in which X and X', independently of each other, each strand for halogen, methyl or nitro, or $R_4$ and $R_5$ may also be linked to form a ring containing 2 or 3 methylene groups, and in which $n$ stands for zero or the integer 1 or 2. The reactions may also be illustrated by the following reaction schemes:

mula (1), in water, than a strong base is added dropwise, for example a 25% sodium hydroxide solution, while maintaining the temperature low, preferably at about 0° C. The alkyl-S-methyl-thiourea carboxylate of formula (3) which has formed need not be isolated.

As chlorofurmates of formula (10), there may be

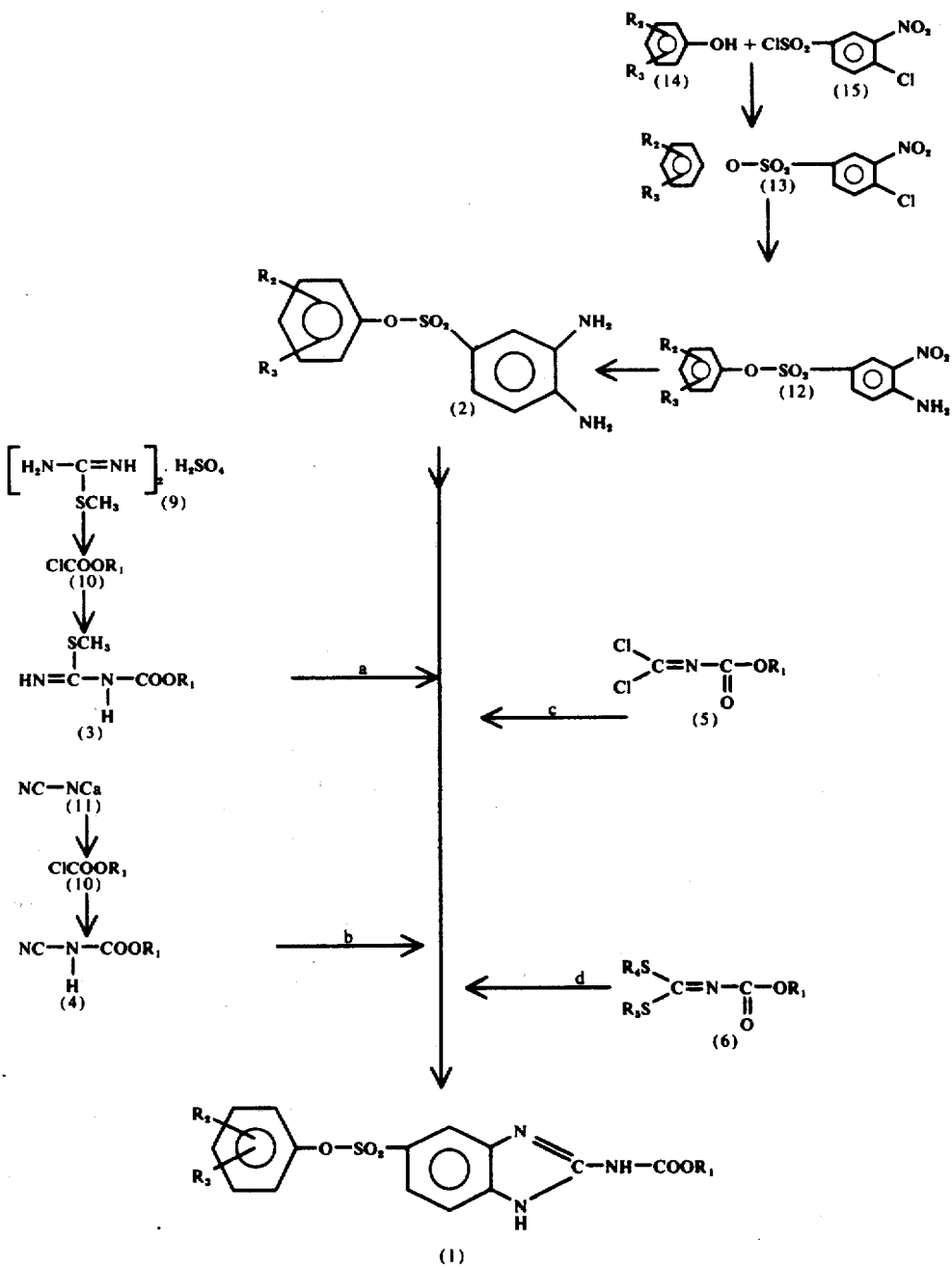

According to reaction method (a), S-methyl-thiourea sulfate of formula (9) is first mixed with a chlorofarmate of formula (10), in which $R_1$ is defined as in formula mentioned, for example,
methyl chloroformate,
ethyl chloroformate,
propyl chloroformate, isopropyl chloroformate,
butyl chloroformate,
isobutyl chloroformate,
tert.butyl chloroformate.

The pH-value of the above-cited reaction mixture is then advantageously adjusted to a range of from 2 to 5, suitably by adding an organic acid, such as acetic acid or lactic acid. The o-phenylene diamine derivative of formula (2) is then added, either in the form of a free base or of the acid addition salt, for example the hydrochloride. In this latter case, it may be advantageous to add an alkali metal salt of an organic acid as a buffer.

As o-phenylene diamine derivatives of formula (2), there are mentioned, for example,
3,4-diamino-benzene sulfonic acid phenyl ester
3,4-diamino-benzene sulfonic acid 4-chloro-phenyl ester
3,4-diamino-benzene sulfonic acid 3-chloro-phenyl ester
3,4-diamino-benzene sulfonic acid 2-chloro-phenyl ester
3,4-diamino-benzene sulfonic acid-2,5-dichloro-phenyl ester
3,4-diamino-benzene sulfonic acid-3,5-dichloro-phenyl ester
3,4-diamino-benzene sulfonic acid-4-bromo-phenyl ester
3,4-diamino-benzene sulfonic acid-3-bromo-phenyl ester
3,4-diamino-benzene sulfonic acid-2-bromo-phenyl ester
3,4-diamino-benzene sulfonic acid 4-methyl-phenyl ester
3,4-diamino-benzene sulfonic acid-3-methyl-phenyl ester
3,4-diamino-benzene sulfonic acid-2-methyl-phenyl ester
3,4-diamino-benzene sulfonic acid-4-tert.butyl-phenyl ester
3,4-diamino-benzene sulfonic acid-2,4-dimethyl-phenyl ester
3,4-diamino-benzene sulfonic acid-2-chloro-4-methyl-phenyl ester
3,4-diamino-benzene sulfonic acid-2-chloro-6-methyl-phenyl ester
3,4-diamino-benzene sulfonic acid-3-chloro-4-methyl-phenyl ester
3,4-diamino-benzene sulfonic acid-3-chloro-6-methyl-phenyl ester
3,4-diamino-benzene sulfonic acid-3-chloro-4-carbethoxy-phenyl ester
3,4-diamino-benzene sulfonic acid-4-chloro-2-methyl-phenyl ester
3,4-diamino-benzene sulfonic acid-4-chloro-3-methyl-phenyl ester
3,4-diamino-benzene sulfonic acid-4-chloro-3,5-dimethyl-phenyl ester
3,4-diamino-benzene sulfonic acid-3,5-bistrifluormethyl-phenyl ester
3,4-diamino-benzene sulfonic acid-4-methoxy-phenyl ester
3,4-diamino-benzene sulfonic acid-3-methoxy-phenyl ester
3,4-diamino-benzene sulfonic acid-2-methoxy-phenyl ester
3,4-diamino-benzene sulfonic acid-4-propoxy-phenyl ester
3,4-diamino-benzene sulfonic acid-4-isopropoxy-phenyl ester
3,4-diamino-benzene sulfonic acid-4-butoxy-phenyl ester
3,4-diamino-benzene sulfonic acid-4-isobutoxy-phenyl ester The reaction components are advantageously reacted at a temperature of from 30° to 100° C within a reaction period of from 30 minutes to 10 hours. Methyl mercaptan is set free as a byproduct. The 2-carbalkoxyamino-benzimidazolyl-5(6) sulfonic acid phenyl esters of formula (1) are isolated in the usual manner, for example by diluting the reaction mixture with water and separating the precipitated product by filtration.

In this manner, there are obtained
2-carbomethoxyamino-5-benzimidazolyl-sulfonic acid phenyl ester
2-carbomethoxyamino-5-benzimidazolyl-sulfonic acid-4-chloro-phenyl ester
2-carbomethoxyamino-5-benzimidazolyl-sulfonic acid-3-chloro-phenyl ester
2-carbomethoxyamino-5-benzimidazolyl-sulfonic acid-2-chloro-phenyl ester
2-carbomethoxyamino-5-benzimidazolyl-sulfonic acid-2,5-dichloro-phenyl ester
2-carbomethoxyamino-5-benzimidazolyl-sulfonic acid-3,5-dichloro-phenyl ester
2-carbomethoxyamino-5-benzimidazolyl-sulfonic acid-4-bromo-phenyl ester
2-carbomethoxyamino-5-benzimidazolyl-sulfonic acid-3-bromo-phenyl ester
2-carbomethoxyamino-5-benzimidazolyl-sulfonic acid-2-bromo-phenyl ester
2-carbomethoxyamino-5-benzimidazolyl-sulfonic acid-4-methyl-phenyl ester
2-carbomethoxyamino-5-benzimidazolyl-sulfonic acid-3-methyl-phenyl ester
2-carbomethoxyamino-5-benzimidazolyl-sulfonic acid-2-methyl-phenyl ester
2-carbomethoxyamino-5-benzimidazolyl-sulfonic acid-4-tert. butyl-phenyl ester
2-carbomethoxyamino-5-benzimidazolyl-sulfonic acid-2,4-dimethyl-phenyl ester
2-carbomethoxyamino-5-benzimidazolyl-sulfonic acid-2-chloro-4-methyl-phenyl ester
2-carbomethoxyamino-5-benzimidazolyl-sulfonic acid-2-chloro-6-methyl-phenyl ester
2-carbomethoxyamino-5-benzimidazolyl-sulfonic acid-3-chloro-4-methyl-phenyl ester
2-carbomethoxyamino-5-benzimidazolyl-sulfonic acid-3-chloro-6-methyl-phenyl ester
2-carbomethoxyamino-5-benzimidazolyl-sulfonic acid-3-chloro-4-carbethoxy-phenyl ester
2-carbomethoxyamino-5-benzimidazolyl-sulfonic acid-4-chloro-2-methyl-phenyl ester
2-carbomethoxyamino-5-benzimidazolyl-sulfonic acid-4-chloro-3-methyl-phenyl ester
2-carbomethoxyamino-5-benzimidazolyl-sulfonic acid-4-chloro-3,5-dimethyl-phenyl ester
2-carbomethoxyamino-5-benzimidazolyl-sulfonic acid-3,5-bis-trifluoromethyl-phenyl ester
2-carbomethoxyamino-5-benzimidazolyl-sulfonic acid-4-methoxy-phenyl ester
2-carbomethoxyamino-5-benzimidazolyl-sulfonic acid-3-methoxy-phenyl ester
2-carbomethoxyamino-5-benzimidazolyl-sulfonic acid-2-methoxy-phenyl ester
2-carbomethoxyamino-5-benzimidazolyl-sulfonic acid-4-propoxy-phenyl ester
2-carbomethoxyamino-5-benzimidazolyl-sulfonic acid-4-isopropoxy-phenyl ester 2-carbomethoxyamino-5-benzimidazolyl-sulfonic acid-4-butoxy-phenyl ester
2-carbomethoxyamino-5-benzimidazolyl-sulfonic acid-4-isobutoxy-phenyl ester
2-carb-ethoxyamino-5-benzimidazolyl-sulfonic acid-phenyl ester
2-carbopropoxyamino-5-benzimidazolyl-sulfonic acid-phenyl ester
2-carbisopropoxyamino-5-benzimidazolyl-sulfonic acid-phenyl ester
2-carbobutoxyamino-5-benzimidazolyl-sulfonic acid-phenyl ester
2-carbisobutoxyamino-5-benzimidazolyl-sulfonic acid-phenyl ester
2-carbo-tert.butoxyamino-5-benzimidazolyl-sulfonic acid phenyl ester.

According to reaction method (b), a chloroformate of formula (10), as also used for method (a), is first added to an aqueous suspension of cyanamide in the form of a salt, advantageously the calcium salt of formula (11), while maintaining the reaction temperature between 40° and 60° C by cooling.

After filtration of dark-colored by-products which have separated, the cyanamide carboxylate of formula (4) is obtained in the filtrate.

The cyanamide carboxylate of formula (4) thus obtained is combined with an o-phenylene diamine derivative of formula (2), and the pH-value of the mixture is adjusted to a range between 1 to 6, preferably 2 to 4, by adding a mineral acid, for example concentrated hydrochloric acid. To complete the reaction, the reaction mixture is advantageously maintained at a temperature of from 30° to 100° C over a period of 30 minutes to 10 hours, depending on the reactivity of the o-phenylene diamine derivative used. After the reaction mixture has been cooled, the precipitated reaction product of formula (1) is isolated by filtration and washing.

The o-phenylene diamine derivative of formula (2) may be used either in the form of a free amine in the manner mentioned above with an alkyl-S-methyl thiourea carboxylate of formula (3) or in the form of an acid addition salt with a suitable inorganic or organic acid, such as hydrochloric acid, sulfuric acid, acetic acid, oxalic acid.

According to the reaction method (c), 1 mol of an o-phenylene-diamine derivative of formula (2) is suitably reacted with 1 mol of an N-dichloromethylene carbamic acid ester of formula (5) in the presence of 2 mols of a base.

As bases, there may be mentioned alkali metal or alkaline earth metal hydroxides, carbonates and hydrogen carbonates, or tertiary organic bases, for example sodium hydroxide, sodium bicarbonate, sodium carbonate, potassium carbonate, potassium bicarbonate, triethylamine, pyridine and methylated pyridines.

The N-dichloromethylene carbamic acid esters of formula (5) may be prepared according to German Offenlegungsschrift No. 1,932,297 by reacting the known dichloromethylene carbamic acid chloride with an alcohol in the presence of an inert organic solvent such as ether; dioxan, tetrahydrofuran, benzene or toluene, at a temperature of from 0° to 40° C.

As examples of N-dichloromethylene carbamic acid esters of formula (5), there may be mentioned N-dichloromethylene carbamic acid methyl ester, as well as the ethyl ester, isopropyl ester, propyl ester, n-butyl ester and sec.-butyl ester thereof.

The reaction temperatures may be varied greatly, generally in the range of from −10° to +60° C, preferably from 0° to 30° C.

According to the reaction method (d), 1 mol of the o-phenylene diamine derivative of formula (2) is advantageously reacted with 1 mol of bis-alkyl or bis-aryl-thiomethylene-amino formiate of formula (6) in an inert solvent, such as tetrahydrofuran, dioxan, isopropyl ether or chloroform, at an elevated temperature, advantageously at the boiling temperature of the solvent used.

According to the invention, it is also possible to prepare the bis-alkyl or bis-aryl-thiomethylene-amino-formate of formula (6) in the reaction vessel from the hydrochloride of imino-thiocarbonic acid ester by adding a choloroformate of formula (10), as it is also used for method (a).

In such a case, use has to be made of an acid binder, for example an organic or inorganic base, such as sodium hydroxide, sodium bicarbonate or triethylamine. As a reaction medium, polar and unpolar solvents are suitable, for example ether, acetone, dioxan, water, dimethylformamide, benzene or cyclohexane. During this reaction, the temperature should advantageously not exceed 20° C.

The bis-alkyl or bis-aryl-thiomethylene-amino-formates may be obtained by reacting corresponding dithio-imino-carbonic acid esters with chloraformates of formula (10) according to the method disclosed in U.S. Pat. No. 3,562,290.

As examples of bis-alkyl or bis-aryl-thiomethylene-amino-formates of formula (6), there are mentioned:
bis-methylthio-methylene-amino-formic acid-methyl ester
bis-methylthio-methylene-amino-formic acid-ethyl ester
bis-methylthio-methylene-amino-formic acid-propyl ester
bis-methylthio-methylene-amino-formic acid-isopropyl ester
bis-methylthio-methylene-amino-formic acid-butyl ester
bis-methylthio-methylene-amino-formic acid-sec.butyl ester
bis-butylthio-methylene-amino-formic acid-methyl ester
methylthio-butylthio-methylene-amino-formic acid-methyl ester
allylthio-cyclohexylthio-methylene-amino-formic acid-methyl ester
methylthio-phenyl-thio-methylene-amino-formic acid-methyl ester
methylthio-(3,4-dichloro-benzyl-thio)-methylene-amino-formic acid-methyl ester or
methylthio-(2-chloro-4-methylthio)-methylene-amino-formic acid methyl ester.

The o-phenylene diamine derivative of formula (2) used as a starting material for the reactions (a) to (d) is obtained by reduction of a corresponding amino-nitro derivative of formula (12), in which $R_2$ and $R_3$ are defined as in formula (1). The reduction may be carried out, for example by hydrogenation in the presence of Raney nickel and a solvent, such as methanol or dimethylformamide, at a temperature of from 20° to 60° C, or by a treatment with reducing agents, such as sodium dithionite.

The amino-nitro derivatives of formula (12) are obtained by reacting the corresponding chloro-nitro compounds of formula (13), in which $R_2$ and $R_3$ are defined as in formula (1), with ammonia in a suitable solvent, such as dioxan or methanol, at an elevated temperature and under elevated pressure. These chloro-nitro compounds of formula (13) again are obtained by reacting 3-nitro-4-chloro-benzene-sulfonic acid chloride of formula (15) with a phenol of formula (14), in which $R_2$ and $R_3$ are defined as in formula (1), in an inert solvent in the presence of a base, such as triethylamine.

The 2-carbalkoxyamino-benzimidazolyl-5(6)-sulfonic acid phenyl esters of the invention are valuable chemotherapeutic agents and are suitable for combating diseases caused by parasites in humans and animals, such as helminths and liver flukes.

They are especially active against a great number of helminths, for example Haemonchus, Trichostrongylus, Ostertagia, Strongyloides, Cooperia, Chabertia, Oesophagostomum, Hyostrongylus, Ankylostoma, Askaris and Heterakis. Especially marked is the activity against gastro-intestinal Strongylides, which most especially infest ruminants. The infestation of animals by these parasites causes great economic damage, so that the compounds of the present invention are mainly used in veterinary drugs.

The compounds of the formula (1) can be administered in doses of from 0.5 to 50 mg per kg of body weight for 1 to 14 days, depending on the individual case.

For oral administration, tablets, dragees, capsules, powder, granules or pastes, which contain the active substances in conjunction with the usual excipients and adjuvants, for example starch, cellulose powder, talcum, magnesium stearate, sugar, gelatin, calcium carbonate, finely divided silicic acid, carboxymethyl cellulose and similar substances, may be used.

For parenteral administration, solutions may be used, for example oily solutions prepared using sesame oil, castor oil or synthetic triglycerides, optionally with the addition of tacopherol as an antioxidant and/or surface-active substances, such as sorbitan fatty acid esters. In addition, aqueous suspensions are used which are prepared using ethoxylated sorbitan fatty acid esters, optionally with an addition of thickeners, such as polyethylene glycol or carboxymethyl cellulose.

The concentrations of the compounds of the present invention in the compositions prepared therewith are preferably in the range of from 2 to 20 % by weight for veterinary drugs; for use as medicaments for humans, the concentrations of the active substances are preferably in the range of from 20 to 80 % by weight.

The activity of the compounds of the invention was determined with the aid of chemotherapeutic investigations made on lambs, each having a weight of about 30 kg, which had been infested for test purposes with larvae of Haemonchus contortus and Trichostrongylus colubriformis respectively. The test animals were kept in tiled boxes which were cleaned thoroughly every day. After the prepatency period (i.e. time between infestation and sexual maturity of the parasites, when secretion of eggs or larvae begins), the number of eggs per gram of excrement was determined by the modified McMaster method according to Wetzel (Tierarztliche Umschau, 6, 209 – 210 (1951)). Immediately after this, the treatment of the sheep was started (generally 4 to 8 animals, at least 2 animals, per active substance). The dosage units of the products of the invention were administered to the animals in the form of a suspension each in 10 ml of a 1% tylose suspension. On the 7th, 14th and 28th day after this treatment, the number of eggs per gram of excrement was again determined according to this above-cited method, and its decrease in percentage as compared to the initial value prior to the treatment was calculated.

The products of the invention have an excellent activity not only when administered per os but also parenterally at doses as low as 2 mg/kg of body weight. Therefore, they are by far superior to comparable benzimidazole derivatives, especially to all the known 2-benzimidazolyl carbamates substituted in 5(6)-position.

The following Examples illustrate the invention.

Process (a)

EXAMPLE 1

60 Grams of a 25% sodium hydroxide solution were added dropwise while cooling with ice at a temperature not exceeding 10° C to a thoroughly stirred mixture of 27.8 g of S-methyl-thiourea sulfate in 44 ml of water and 13 ml of methyl chloroformate. Stirring was continued for half an hour, and then a mixture of 10 ml of glacial acetic acid and 100 ml of water was added. Subsequently, 24.2 g of 3,4-diamino-benzene-sulfonic acid phenyl ester dissolved in 100 ml of isopropanol were added, and the mixture was refluxed for 2 hours, whereupon a solid began to precipitate. The solid was suction-filtered, carefully washed with methanol and then with water and, after drying, 19 g of 2-carbomethoxyamino-5-benzimidazolyl sulfonic acid phenyl ester were obtained. The crude product was purified by dissolving it in 250 ml of dioxan, filtering it with charcoal and adding 50 ml of water to the filtrate. The yield of the analytically pure product was 14 g, having a decomposition point of 242° C.

3,4-diamino-benzene-sulfonic acid phenyl ester was prepared by hydrogenating 27 g of 3-nitro-4-amino-benzene-sulfonic acid phenyl ester in 300 ml of methyl glycol with Raney nickel at atmospheric pressure and room temperature. The catalyst was separated by suction-filtration, and upon concentration, the 3,4-diamino-benzene sulfonic acid phenyl ester was obtained as a crude product in the form of 25 g of a dark-colored oil which could directly be used for ring closure.

To prepare 3-nitro-4-amino-benzene sulfonic acid phenyl ester 54 g of 3-nitro-4-chloro-benzene sulfonic acid phenyl ester in 500 ml of dioxan were maintained at 50° C for 5 hours at an excess pressure of 5 atmospheres of gaseous ammonia, then the solvent was removed in vacuo. The residue was combined with 200 ml of a mixture of equal parts of methanol and water, whereupon a solid precipitated after a short time, which was suction-filtered. After repeated recrystallization from methanol and then from benzene, 28 g of 3-nitro-4-aminobenzene sulfonic acid phenyl ester were obtained, m.p. 104° C.

3-Nitro-4-chlorobenzene sulfonic acid phenyl ester was obtained by mixing 51 g of 3-nitro-4-chlorobenzene sulfonic acid chloride with 18.8 g of phenol in 120 ml of acetone, and 28 ml of triethylamine were added dropwise while cooling at an internal temperature not exceeding 10° C. Stirring was continued for some hours at room temperature, and water was then added, whereupon an oil separated which was worked up with ether. Upon recrystallization from methanol, 54 g of 3-nitro-4-chloro-benzene sulfonic acid phenyl ester were obtained, m.p. 71° C.

Using correspondingly modified starting products, the following compounds were prepared in an analogous manner:

2. Via 3-nitro-4-chloro-benzenesulfonic acid-4-chlorophenyl ester, m.p. 84° C
   and 3-nitro-4-amino-benzenesulfonic acid-4-chlorophenyl ester, m.p. 156° C
   and 3,4-diamino-benzenesulfonic acid-4-chloro-phenyl ester, the 2-carbomethoxyamino-5-benzimidazolylsulfonic acid-4-chloro-phenyl ester, m.p. 250° C (decomp.).

3. Via 3-nitro-4-chloro-benzenesulfonic acid-3-chlorophenyl ester, m.p. 68° C
   and 3-nitro-4-amino-benzenesulfonic acid-3-chlorophenyl ester, m.p. 138° C
   and 3,4-diamino-benzenesulfonic acid-3-chloro-phenyl ester, m.p. 84° C,
   the 2-carbomethoxyamino-5-benzimidazolylsulfonic acid-3-chloro-phenyl ester, m.p. 234° C, (decomp.).

4. Via 3-nitro-4-chloro-benzenesulfonic acid-2-chlorophenyl ester
   and 3-nitro-4-amino-benzenesulfonic acid-2-chlorophenyl ester
   and 3,4-diamino-benzenesulfonic acid-2-chloro-phenyl ester, the 2-carbomethoxyamino-5-benzimidazolylsulfonic acid-2-chloro-phenyl ester.

5. Via 3-nitro-4-chloro-benzenesulfonic acid-2,5-dichloro-phenyl ester
   and 3-nitro-4-amino-benzenesulfonic acid-2,5-dichloro-phenyl ester
   and 3,4-diamino-benzenesulfonic acid-2,5-dichloro-phenyl-ester,
   the 2-carbomethoxyamino-5-benzimidazolylsulfonic acid-2,5-dichloro-phenyl ester.

6. Via 3-nitro-4-chloro-benzenesulfonic acid-3,5-dichloro-phenyl ester, m.p. 104° C
   and 3-nitro-4-amino-benzenesulfonic acid-3,5-dichloro-phenyl ester, m.p. 164° C
   and 3,4-diamino-benzenesulfonic acid-3,5-dichlorophenyl ester, mp. 116° C,
   the 2-carbomethoxyamino-5-benzimidazolylsulfonic acid-3,5-dichloro-phenyl ester, m.p. 250° C (decomp.).

7. Via 3-nitro-4-chloro-benzenesulfonic acid-4-bromophenyl ester
   and 3-nitro-4-amino-benzensulfonic acid-4-bromophenyl ester
   and 3,4-diamino-benzenesulfonic acid-4-bromo-phenyl ester,
   the 2-carbomethoxyamino-5-benzimidazolylsulfonic acid-4-bromo-phenyl ester.

8. Via 3-nitro-4-chloro-benzenesulfonic acid-3-bromophenyl ester, m.p. 72° C
   and 3-nitro-4-amino-benzenesulfonic acid-3-bromophenyl ester, m.p. 141° C
   and 3,4-diamino-benzenesulfonic acid-3-bromo-phenyl ester, m.p. 94° C,
   the 2-carbomethoxyamino-5-benzimidazolylsulfonic acid-3-bromo-phenyl ester, m.p. 242° C (decomp.).

9. Via 3-nitro-4-chloro-benzenesulfonic acid-2-bromophenyl ester
   and 3-nitro-4-amino-benzenesulfonic acid-2-bromophenyl ester
   and 3,4-diamino-benzenesulfonic acid-2-bromo-phenyl ester,
   the 2-carbomethoxyamino-5-benzimidazolyl-sulfonic acid-2-bromo-phenyl ester.

10. Via 3-nitro-4-chloro-benzenesulfonic acid-4-methyl-phenyl-ester, m.p. 68° C
    and 3-nitro-4-amino-benzenesulfonic acid-4-methylphenyl ester, m.p. 135° C
    and 3,4-diamino-benzenesulfonic acid-4-methylphenyl ester,
    the 2-carbomethoxyamino-5-benzimidazolylsulfonic acid-4-methyl-phenyl ester, m.p. 240° C, (decomp.).

11. Via 3-nitro-4-chloro-benzenesulfonic acid-3-methyl-phenyl-ester, m.p. 60° C
    and 3-nitro-4-amino-benzenesulfonic acid-3-methylphenyl-ester, m.p. 138° C
    and 3,4-diamino-benzenesulfonic acid-3-methylphenyl-ester, m.p. 84° C,
    the 2-carbomethoxyamino-5-benzimidazolylsulfonic acid-3-methyl-phenyl ester, m.p. 234° C (decomp.).

12. Via 3-nitro-4-chloro-benzenesulfonic acid-2-methyl-phenyl ester
    and 3-nitro-4-amino-benzenesulfonic acid-2-methylphenyl ester
    and 3,4-diamino-benzenesulfonic acid-2-methylphenyl ester,
    the 2-carbomethoxyamino-5-benzimidazolylsulfonic acid-2-methyl-phenyl ester.

13. Via 3-nitro-4-chloro-benzenesulfonic acid-4-tert.butyl-phenyl ester
    and 3-nitro-4-amino-benzenesulfonic acid-4-tert.butyl-phenyl ester
    and 3,4-diamino-benzenesulfonic acid-4-tert.butylphenyl ester,
    the 2-carbomethoxyamino-5-benzimidazolylsulfonic acid-tert.butyl-phenyl ester.

14. Via 3-nitro-4-chloro-benzenesulfonic acid-2,4-dimethyl-phenyl ester
    and 3-nitro-4-amino-benzenesulfonic acid-2,4dimethyl-phenyl ester
    and 3,4-diamino-benzenesulfonic acid-2,4-dimethyl phenyl ester,
    the 2-carbomethoxyamino-5-benzimidazolylsulfonic acid-2,4-dimethyl-phenyl ester.

15. Via 3-nitro-4-chloro-benzenesulfonic acid-2-chloro-4-methyl-phenyl ester
    and 3-nitro-4-amino-benzenesulfonic acid-2-chloro-4-methyl-phenyl ester
    and 3,4-diamino-benzenesulfonic acid-2-chloro-4-methyl-phenyl ester,
    the 2-carbomethoxyamino-5-benzimidazolylsulfonic acid-2-chloro-4-methyl-phenyl ester.

16. Via 3-nitro-4-chloro-benzenesulfonic acid-2-chloro-6-methyl-phenyl ester
    and 3-nitro-4-amino-benzenesulfonic acid-2-chloro-6-methyl-phenyl ester
    and 3,4-diamino-benzenesulfonic acid-2-chloro-6-methyl-phenyl ester,
    the 2-carbomethoxyamino-5-benzimidazolylsulfonic acid-2-chloro-6-methyl-phenyl ester.

17. Via 3-nitro-4-chloro-benzenesulfonic acid-3-chloro-4-methyl-phenyl ester
    and 3-nitro-4-amino-benzenesulfonic acid-3-chloro-4-methyl-phenyl ester
    and 3,4-diamino-benzenesulfonic acid-3-chloro-4-methyl-phenyl ester,
    the 2-carbomethoxyamino-5-benzimidazolylsulfonic acid-3-chloro-4-methyl-phenyl ester.

18. Via 3-nitro-4-chloro-benzenesulfonic acid-3-chloro-6-methyl-phenyl ester
    and 3-nitro-4-amino-benzenesulfonic acid-3-chloro-6-methyl-phenyl ester
    and 3,4-diamino-benzenesulfonic acid-3-chloro-6-methyl-phenyl ester, the 2-carbomethoxyamino-5-benzimidazolylsulfonic acid-3-chloro-6-methyl-phenyl ester.

19. Via 3-nitro-4-chloro-benzenesulfonic acid-3-chloro-4-carbethoxy-phenyl ester
and 3-nitro-4-amino-benzenesulfonic acid-3-chloro-4-carbethoxy-phenyl ester
and 3,4-diamino-benzenesulfonic acid-3-chloro-4-carbethoxy-phenyl ester,
the 2-carbomethoxyamino-5-benzimidazolylsulfonic acid-3-chloro-4-carbethoxy-phenyl ester.

20. Via 3-nitro-4-chloro-benzenesulfonic acid-4-chloro-2-methyl-phenyl ester
and 3-nitro-4-amino-benzenesulfonic acid-4-chloro-2-methyl-phenyl ester
and 3,4-diamino-benzenesulfonic acid-4-chloro-2-methyl-phenyl ester,
the 2-carbomethoxyamino-5-benzimidazolylsulfonic acid-4-chloro-2-methyl-phenyl ester.

21. Via 3-nitro-4-chloro-benzenesulfonic acid-4-chloro-3-methyl-phenyl ester
and 3-nitro-4-amino-benzenesulfonic acid-4-chloro-3-methyl-phenyl ester
and 3,4-diamino-benzenesulfonic acid-4-chloro-3-methyl-phenyl ester,
the 2-carbomethoxyamino-5-benzimidazolylsulfonic acid-4-chloro-3-methyl-phenyl ester.

22. Via 3-nitro-4-chloro-benzenesulfonic acid-4-chloro-3,5-dimethyl-phenyl ester
and 3-nitro-4-amino-benzenesulfonic acid-4-chloro-3,5-dimethyl-phenyl ester
and 3,4-diamino-benzenesulfonic acid-4-chloro-3,5-dimethyl-phenyl ester,
the 2-carbomethoxyamino-5-benzimidazolylsulfonic acid-4-chloro-3,5-dimethyl-phenyl ester.

23. Via 3-nitro-4-chloro-benzenesulfonic acid-3,5-bistrifluoro-methyl-phenyl ester
and 3-nitro-4-amino-benzenesulfonic acid-3,5-bistrifluoro-methyl-phenyl ester
and 3,4-diamino-benzenesulfonic acid-3,5-bistrifluoro-methyl-phenyl ester,
the 2-carbomethoxyamino-5-benzimidazolylsulfonic acid-3,5-bistrifluoro-methyl-phenyl ester.

24. Via 3-nitro-4-chloro-benzenesulfonic acid-4-methoxy-phenyl ester, m.p. 88° C
and 3-nitro-4-amino-benzenesulfonic acid-4-methoxy-phenyl-ester, m.p. 140° C
and 3,4-diamino-benzenesulfonic acid-4-methoxy-phenyl ester,
the 2-carbomethoxyamino-5-benzimidazolylsulfonic acid-4-methoxy-phenyl ester, m.p. 228° C, (decomp.).

25. Via 3-nitro-4-chloro-benzenesulfonic acid-3-methoxy-phenyl ester (oil)
and 3-nitro-4-amino-benzenesulfonic acid-3-methoxy-phenyl-ester, m.p. 116° C
and 3,4-diamino-benzenesulfonic acid-3-methoxy-phenyl ester (oil),
the 2-carbomethoxyamino-5-benzimidazolylsulfonic acid-3-methoxy-phenyl ester, m.p. 227° C (decomp.).

26. Via 3-nitro-4-chloro-benzenesulfonic acid-2-methoxy-phenyl ester
and 3-nitro-4-amino-benzenesulfonic acid-2-methoxy-phenyl ester
and 3,4-diamino-benzenesulfonic acid-2-methoxy-phenyl ester,
the 2-carbomethoxyamino-5-benzimidazolylsulfonic acid-2-methoxy-phenyl ester.

27. Via 3-nitro-4-chloro-benzenesulfonic acid-4-propoxy-phenyl ester
and 3-nitro-4-amino-benzenesulfonic acid-4-propoxy-phenyl ester
and 3,4-diamino-benzenesulfonic acid-4-propoxy-phenyl ester, the 2-carbomethoxyamino-5-benzimidazolylsulfonic acid-4-propoxy-phenyl ester.

28. Via 3-nitro-4-chloro-benzenesulfonic acid-4-isopropoxy-phenyl ester
and 3-nitro-4-amino-benzenesulfonic acid-4-isopropoxy-phenyl ester
and 3,4-diamino-benzenesulfonic acid-4-isopropoxy-phenyl ester,
the 2-carbomethoxya mino-5-benzimidazolylsulfonic acid-4-isopropoxy-phenyl ester.

29. Via 3-nitro-4-chloro-benzenesulfonic acid-4-butoxy-phenyl ester
and 3-nitro-4-amino-benzenesulfonic acid-4-butoxy-phenyl ester
and 3,4-diamino-benzenesulfonic acid-4-butoxy-phenyl ester, the 2-carbomethoxyamino-5-benzimidazolylsulfonic acid-4-butoxy-phenyl ester.

30. Via 3-nitro-4-chloro-benzenesulfonic acid-3-ethoxy-phenyl ester (oil)
and 3-nitro-4-amino-benzenesulfonic acid-3-ethoxy-phenyl ester, m.p. 86° C
and 3,4-diamino-benzenesulfonic acid-3-ethoxy-phenyl ester (oil),
the 2-carbomethoxyamino-5-benzimidazolylsulfonic acid-3-ethoxy-phenyl ester, m.p. 212° C, (decomp.).

31. Via 3-nitro-4-chloro-benzenesulfonic acid-4-isobutoxy-phenyl ester
and 3-nitro-4-amino-benzenesulfonic acid-4-isobutoxy-phenyl ester
and 3,4-diamino-benzenesulfonic acid-4-isobutoxy-phenyl ester,
the 2-carbomethoxyamino-5-benzimidazolylsulfonic acid-4-isobutoxy-phenyl ester.

32. Via 3-nitro-4-chloro-benzenesulfonic acid-3-cyano-phenyl ester, m.p. 118° C
and 3-nitro-4-amino-benzenesulfonic acid-3-cyano-phenyl ester, m.p. 183° C
and 3,4-diamino-benzenesulfonic acid-3-cyano-phenyl ester,
the 2-carbomethoxyamino-5-benzimidazolylsulfonic acid-3-cyano-phenyl ester, m.p. 265° C, (decomp.).

33. Via 3-nitro-4-chloro-benzenesulfonic acid-phenyl ester
and 3-nitro-4-amino-benzenesulfonic acid-phenyl ester
and 3,4-diamino-benzenesulfonic acid-phenyl ester,
the 2-carbethoxyamino-5-benzimidazolylsulfonic acid phenyl ester.

34. Via 3-nitro-4-chloro-benzenesulfonic acid-phenyl ester
and 3-nitro-4-amino-benzenesulfonic acid-phenyl ester
and 3,4-diamino-benzenesulfonic acid-phenyl ester,
the 2-carbopropoxyamino-5-benzimidazolylsulfonic acid-phenyl ester.

35. Via 3-nitro-4-chloro-benzenesulfonic acid-phenyl ester
and 3-nitro-4-amino-benzenesulfonic acid-phenyl ester
and 3,4-diamino-benzenesulfonic acid-phenyl ester,
the 2-carboisopropoxyamino-5-benzimidazolylsulfonic acid-phenyl ester.

36. Via 3-nitro-4-chloro-benzenesulfonic acid-phenyl ester and 3-nitro-4-amino-benzenesulfonic acid-phenyl ester and 3,4-diamino-benzenesulfonic acid-phenyl ester, the 2-carbobutoxyamino-5-benzimidazolylsulfonic acid-phenyl ester.

37. Via 3-nitro-4-chloro-benzenesulfonic acid-phenyl ester and 3-nitro-4-amino-benzenesulfonic acid-phenyl ester and 3,4-diamino-benzenesulfonic acid-phenyl ester, the 2-carboisobutoxyamino-5-benzimidazolylsulfonic acid-phenyl ester.

38. Via 3-nitro-4-chloro-benzenesulfonic acid-phenyl ester and 3-nitro-4-amino-benzenesulfonic acid-phenyl ester and 3,4-diamino-benzenesulfonic acid-phenyl ester, the 2-carbo-tert.butoxyamino-5-benzimidazolyl-sulfonic acid-phenyl ester.

39. Via 3-nitro-4-chloro-benzenesulfonic acid 3-trifluoromethyl phenyl ester, m.p. 65° C and 3-nitro-4-amino-benzenesulfonic acid 3-trifluoromethyl phenyl ester, m.p. 132° C and 3,4-diamino-benzenesulfonic acid 3-trifluoromethyl phenyl ester the 2-carbomethoxyamino-5-benzimidazolyl-sulfonic acid 3-trifluoromethyl phenyl ester, m.p. 250° C (with decomposition).

Process (b)

EXAMPLE 40

To a solution of 42 g of cyanamide in 210 ml of water, 90 g of chloroformic acid methyl ester and 218 g of a 33% sodium hydroxide solution were added. The mixture was stirred for 1.5 hours at a temperature of 30° to 35° C, then a solution of 213 g of 3,4-diamino-benzenesulfonic acid phenyl ester in 1 l of isopropanol was added, whereupon the temperature was raised to 80° C. After addition of 800 ml of glacial acetic acid, the reaction mixture was maintained at 90° C for another 3 to 4 hours. Then it was allowed to cool and stored overnight in a refrigerator. The precipitated 2-carbomethoxyamino-5-benzimidazolyl-sulfonic acid phenyl ester was suction-filtered and washed with isopropanol and water. For purification the crude product was dissolved in dioxan, filtered with charcoal and combined with water. Yield: 80 g, decomposition point: 242° C.

The 3,4-diamino-benzenesulfonic acid phenyl ester was obtained according to Example 1 via the intermediates 3-nitro-4-chlorobenzenesulfonic acid phenyl ester and 3-nitro-4-amino-benzenesulfonic acid phenyl ester which are likewise disclosed in Example 1. In an analogous manner, the following compounds were prepared using correspondingly modified starting materials:

41. Via 3-nitro-4-chloro-benzene-sulfonic acid-3-chloro-phenyl ester, m.p. 68° C
and 3-nitro-4-amino-benzene-sulfonic acid-3-chloro-phenyl ester, m.p. 138° C
and 3,4-diamino-benzene-sulfonic acid-3-chloro-phenyl ester, m.p. 84° C
the 2-carbomethoxyamino-5-benzimidazolyl-sulfonic acid-3-chlorophenyl ester (identical with Example 3), m.p. 234° C (decomposition).

42. Via 3-nitro-4-chloro-benzene-sulfonic acid-3-bromo-phenyl ester, m.p. 72° C
and 3-nitro-4-amino-benzene-sulfonic acid-3-bromo-phenyl-ester, m.p. 141° C
and 3,4-diamino-benzene-sulfonic acid-3-bromo-phenyl ester m.p. 94° C
the 2-carbomethoxyamino-5-benzimidazolyl-sulfonic acid acid-3-bromo-phenyl ester (identical with Example 8), m.p. 242° C (decomposition).

43. Via 3-nitro-4-chloro-benzene-sulfonic acid-3-methyl-phenyl ester, m.p. 60° C
and 3-nitro-4-amino-benzene-sulfonic acid-3-methyl phenyl ester, m.p. 138° C
and 3,4-diamino-benzene-sulfonic acid-3-methyl-phenyl ester, m.p. 84° C
the 2-carbomethoxyamino-5-benzimidazolyl-sulfonic acid-3-methyl-phenyl ester (identical with Example 11), m.p. 234° C (decomposition).

44. Via 3-nitro-4-chloro-benzene sulfonic acid-3-methoxy-phenyl ester (oil)
and 3-nitro-4-amino-benzene-sulfonic acid-3-methoxy-phenyl ester, m.p. 116° C
and 3,4-diamino-benzene-sulfonic acid-3-methoxy-phenyl ester (oil)
the 2-carbomethoxyamino-5-benzimidazolyl-sulfonic acid-3-methoxy-phenyl ester (identical with Example 25), m.p. 227° C (decomposition).

45. Via 3-nitro-4-chloro-benzene-sulfonic acid-3-ethoxy-phenyl ester (oil)
and 3-nitro-4-amino-benzene-sulfonic acid-3-ethoxy-phenyl ester, m.p. 86° C
and 3,4-diamino-benzene-sulfonic acid-3-ethoxy-phenyl ester (oil)
the 2-carbomethoxyamino-5-benzimidazolyl-sulfonic acid-3-ethoxy-phenyl ester (identical with Example 30), m.p. 212° C (decomposition).

46. Via 3-nitro-4-chloro-benzene-sulfonic acid-3-trifluoro-methyl-phenyl ester, m.p. 65° C
and 3-nitro-4-amino-benzene-sulfonic acid-3-trifluoro-methyl-phenyl ester, m.p. 132° C
and 3,4-diamino-benzene-sulfonic acid-3-trifluoromethyl-phenyl ester
the 2-carbomethoxyamino-5-benzimidazolyl-sulfonic acid-3-trifluoromethyl-phenyl ester, m.p. 250° C (decomposition).

Process (c)

EXAMPLE 47

26.4 Grams of 3,4-diamino-benzenesulfonic acid phenyl ester, 20.2 g of triethylamine and 300 ml of chloroform were mixed and a solution of 15.6 g of N-dichloromethylene carbamic acid methyl ester in 50 ml of chloroform was slowly added while stirring, the maximum temperature being 20° C. Stirring was continued for 1 hour, the precipitate formed was suctionfiltered and washed with chloroform.

For purification, the crude product was dissolved in dioxan, filtered with charcoal and combined with water, After suction-filtration, washing and drying, 5 g of 2-carbomethoxy-amino-5-benzimidazolyl-sulfonic acid phenyl ester having a decomposition point of 242° C were obtained.

The 3,4-diamino-benzenesulfonic acid phenyl ester was obtained as in Example 1 via the intermediate 3-nitro-4-chlorobenzene-sulfonic acid phenyl ester and 3-nitro-4-amino-benzene-sulfonic acid phenyl ester which are likewise disclosed in Example 1.

In an analogous manner, the following compounds were prepared using correspondingly modified starting materials:

48. Via 3-nitro-4-chloro-benzene-sulfonic acid-3-chloro-phenyl ester, m.p. 68° C
and 3-nitro-4-amino-benzene-sulfonic acid-3-chlorophenyl ester, m.p 138° C
and 3,4-diamino-benzene-sulfonic acid-3-chlorophenyl ester, m.p. 84° C
the 2-carbomethoxyamino-5-benzimidazolyl-sulfonic acid-3-chloro-phenyl ester identical with Example 3), m.p. 234° C (decomposition).

49. Via 3-nitro-4-chloro-benzene-sulfonic acid-3-bromo-phenyl ester, m.p. 72° C
and 3-nitro-4-chloro-benzene-sulfonic acid-3-bromo-phenyl ester, m.p. 141° C.
and 3,4-diamino-benzene-sulfonic acid-3-bromo-phenyl ester, m.p. 94° C
the 2-carbomethoxyamino-5-benzimidazolyl-sulfonic acid-3-bromo-phenyl ester (identical with Example 8), m.p. 242° C (decomposition).

50. Via 3-nitro-4-chloro-benzene-sulfonic acid-3-methyl phenyl ester, m.p. 60° C
and 3-nitro-4-amino-benzene-sulfonic acid-3-methyl-phenyl ester, m.p. 138° C
and 3,4-diamino-benzene-sulfonic acid-3-methyl phenyl ester, m.p. 84° C
the 2-carbomethoxyamino-5-benzimidazolyl-sulfonic acid-3-methyl-phenyl ester (identical with Example 11), m.p. 234° C (decomposition).

51. Via 3-nitro-4-chloro-benzene-sulfonic acid-3-methoxy-phenyl ester (oil)
and 3-nitro-4-amino-benzene-sulfonic acid-3-methoxy-phenyl ester, m.p. 116° C
and 3,4-diamino-benzene-sulfonic acid-3-methoxy-phenyl ester (oil)
the 2-carbomethoxyamino-5-benzimidazolyl-sulfonic acid-3-methoxy-phenyl ester (identical with Example 25), m.p. 227° C (decomposition).

52. Via 3-nitro-4-chloro-benzene sulfonic acid-3-ethoxy-phenyl ester (oil)
and 3-nitro-4-amino-benzene-sulfonic acid-3-ethoxy-phenyl ester, m.p. 86° C
and 3,4-diamino-benzene-sulfonic acid-3-ethoxy-phenyl ester (oil)
the 2-carbomethoxyamino-5-benzimidazolyl-sulfonic acid-3-ethoxy-phenyl ester (identical with Example 30), m.p. 212° C (decomposition).

53. Via 3-nitro-4-chloro-benzene-sulfonic acid-3-trifluoro-methyl-phenyl ester, m.p. 65° C
and 3-nitro-4-amino-benzene-sulfonic acid-3-trifluoro-methyl-phenyl ester, m.p. 132° C
and 3,4-diamino-benzene-sulfonic acid-3-trifluoromethyl-phenyl ester
the 2-carbomethoxyamino-5-benzimidazolyl-sulfonic acid-3-trifluoromethyl phenyl ester, m.p. 250° C (decomposition), (identical with Example 39).

Process (d)

EXAMPLE 54

17.9 Grams of bis-methylthio-methylene aminoformic acid methyl ester were added to 26.4 g of 3,4-diamino-benzenesulfonic acid phenyl ester in 200 ml of tetrahydrofuran, and the mixture was refluxed for 3 hours. It was then allowed to cool and the 2-carbomethoxyamino-5-benzimidazolyl-sulfonic acid phenyl ester was suction-filtered, dissolved in dioxan, filtered with charcoal and precipitated with water to purify it. Yield: 12 g, decomposition point: 242° C.

The 3,4-diamino-benzenesulfonic acid phenyl ester was obtained as in Example 1 via the intermediates 3-nitro-4-chloro-benzene-sulfonic acid phenyl ester and 3-nitro-4-amino-benzene-sulfonic acid phenyl ester which are disclosed likewise in Example 1.

EXAMPLE 55

To a cooled solution of 19.7 g of imino-dithiocarbonic acid methyl ester hydrochloride and 12.5 g of chloroformic acid methyl ester in 50 ml of water, a 10% sodium hydroxide solution was added dropwise, while taking care that the temperature did not exceed 10° C. As soon as the pH was adjusted to 7.5, 26.4 g of 3,4-diamino-benzenesulfonic acid phenyl ester in 50 ml of glacial acetic acid were added, and the mixture was refluxed for 2 hours while stirring. It was allowed to cool, and the 2-carbomethoxyamino-5-benzimidazolylsulfonic acid phenyl ester formed was suction-filtered. It was identical in its properties with the reaction product disclosed in Example 54.

In an analogous manner, the following compounds were prepared using correspondingly modified starting materials:

56. Via 3-nitro-4-chloro-benzene-sulfonic acid-3-chloro-phenyl ester, m.p. 68° C
and 3-nitro-4-amino-benzene-sulfonic acid-3-chloro-phenyl ester, m.p. 138° C
and 3,4-diamino-benzene-sulfonic acid-3-chloro-phenyl ester, m.p. 84° C
the 2-carbomethoxyamino-5-benzimidazolyl-sulfonic acid-3-chloro-phenyl ester (identical with Example 3) m.p. 234° C (decomposition).

57. Via 3-nitro-4-chloro-benzene-sulfonic acid-3-bromo-phenyl ester, m.p. 72° C
and 3-nitro-4-amino-benzene-sulfonic acid-3-bromo-phenyl ester, m.p. 141° C
and 3,4-diamino-benzene-sulfonic acid-3-bromo-phenyl ester, m.p. 94° C
the 2-carbomethoxyamino-5-benzimidazolyl-sulfonic acid-3-bromo-phenyl ester (identical with Example 8), m.p. 242° C (decomposition).

58. Via 3-nitro-4-chloro-benzene-sulfonic acid-3-methyl-phenyl ester, m.p. 60° C
and 3-nitro-4-amino-benzene-sulfonic acid-3-methyl-phenyl ester, m.p. 138° C
and 3,4-diamino-benzene-sulfonic acid-3-methyl-phenyl ester, m.p. 84° C
the 2-carbomethoxyamino-5-benzimidazolyl-sulfonic acid-3-methyl-phenyl ester (identical with Example 11), m.p. 234° C (decomposition).

59. Via 3-nitro-4-chloro-benzene-sulfonic acid-3-methoxy-phenyl ester (oil)
and 3-nitro-4-amino-benzene-sulfonic acid-3-methoxy-phenyl ester, m.p. 116° C
and 3,4-diamino-benzene-sulfonic acid-3-methoxy-phenyl ester (oil)
the 2-carbomethoxyamino-5-benzimidazolyl-sulfonic acid-3-methoxy phenyl ester (identical with Example 25) m.p. 227° C (decomposition).

60. Via 3-nitro-4-chloro-benzene-sulfonic acid-3-ethoxy-phenyl ester (oil)
and 3-nitro-4-amino-benzene-sulfonic acid-3-ethoxy-phenyl ester, m.p. 86° C
and 3,4-diamino-benzene-sulfonic acid-3-ethoxy-phenyl ester (oil)
the 2-carbomethoxyamino-5-benzimidazolyl-sulfonic acid-3-ethoxy-phenol ester (identical with Example 30) m.p. 212° C (decomposition).

61. Via 3-nitro-4-chloro-benzene-sulfonic acid-3-trifluoro-methyl-phenyl ester, m.p. 65° C
and 3-nitro-4-amino-benzene-sulfonic acid-3-trifluoromethyl-phenyl ester, m.p. 132° C
and 3,4-diamino-benzene-sulfonic acid-3-trifluoromethyl-phenyl ester
the 2-carbomethoxyamino-5-benzimidazolyl-sulfonic acid-3-trifluoromethyl-phenyl ester, m.p. 250° C (decomposition) (identical with Example 39).

We claim:

1. A 2-carbalkoxyamino benzimidazolyl-5(6) sulfonic acid phenyl ester of the formula

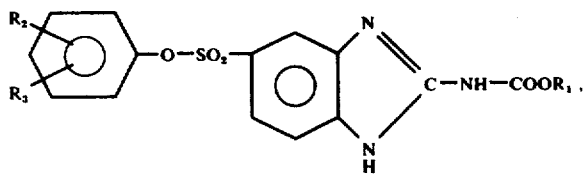

in which $R_1$ stands for alkyl having 1 to 4 carbon atoms, $R_2$ and and $R_3$, independently of each other, each stand for hydrogen, hydroxy, alkoxy having 1 to 4 carbon atoms, halogen, trifluoromethyl, alkyl having 1 to 4 carbon atoms, carbalkoxy having 1 to 4 carbon atoms in the alkoxy moiety, or cyano.

2. A compound as claimed in claim 1, wherein $R_1$ is methyl, $R_2$ is hydrogen, and $R_3$ is hydrogen, chlorine, bromine, trifluoromethyl, methyl, ethyl, methoxy or ethoxy.

3. A compound as claimed in claim 1, wherein $R_1$ is methyl, and $R_2$ and $R_3$ each are hydrogen.

4. A compound as claimed in claim 1, wherein $R_1$ is methyl, $R_2$ is hydrogen and $R_3$ is chlorine.

5. A compound as claimed in claim 1, wherein $R_1$ is methyl, $R_2$ is hydrogen and $R_3$ is bromine.

6. A compound as claimed in claim 1, wherein $R_1$ is methyl, $R_2$ is hydrogen and $R_3$ is methyl.

7. A compound as claimed in claim 1, wherein $R_1$ is methyl, $R_2$ is hydrogen and $R_3$ is methoxy.

8. A compound as claimed in claim 1, wherein $R_1$ is methyl, $R_2$ is hydrogen and $R_3$ is ethoxy.

9. A compound as claimed in claim 1, wherein $R_1$ is methyl, $R_2$ is hydrogen and $R_3$ is trifluoromethyl.

10. A pharmaceutical composition for combatting helminths and liver flukes, said composition containing an effective amount of a compound as in claim 1 in admixture or conjunction with a pharmaceutically acceptable carrier.

11. A method for combatting helminths and liver flukes in humans and animals which comprises administering an effective amount of a compound as in claim 1.

* * * * *